United States Patent [19]

Corley et al.

[11] Patent Number: 4,940,813

[45] Date of Patent: Jul. 10, 1990

[54] RESOLUTION OF A CARBOXYLIC ACID

[75] Inventors: Edward G. Corley, Old Bridge; Robert D. Larsen, Monmouth Junction; Edward J. J. Grabowski, Westfield; Paul Reider, Westfield, all of N.J.

[73] Assignee: Merck & Co., Inc., Rahway, N.J.

[21] Appl. No.: 331,145

[22] Filed: Mar. 31, 1989

[51] Int. Cl.$^5$ .................... C07C 69/612; C07B 55/00
[52] U.S. Cl. .................... 560/103; 560/110; 560/1; 560/9; 560/15; 560/47; 560/49; 560/60; 560/101; 560/104; 560/105; 560/66; 560/83; 560/88; 560/169; 560/184; 560/187; 560/179; 560/219; 549/319; 556/436; 562/401; 562/496; 562/579; 562/606
[58] Field of Search ............... 562/401, 496, 579, 591, 562/606; 549/319; 556/436; 560/1, 9, 15, 19, 47, 49, 60, 105, 101, 104, 66, 83, 88, 169, 184, 187, 205, 219, 179

[56] References Cited

U.S. PATENT DOCUMENTS 4,529,810  7/1985  Stoutamire ................... 562/496
4,691,020  9/1987  Ruechardt et al. ............ 546/341

OTHER PUBLICATIONS

U. Salz & C. Ruchardt, *Tetrahedron Letters*, 23, No. 39, 4017 (1982).
R. D. Larsen et al., *J. Am. Chem. Soc.*, III, 7650 (1989).
G. Bellucci et al., *Gazz.Chim.Ital.*, 118, 451 (1988).

*Primary Examiner*—Glennon H. Hollrah
*Assistant Examiner*—Mark W. Russell
*Attorney, Agent, or Firm*—Melvin Winokur; Joseph F. DiPrima

[57] ABSTRACT

A process is described for the preparation of an optically active carboxylic acid or ester derivative thereof from a ketene and an optically active α-hydroxyester or an α-hydroxy amide.

22 Claims, No Drawings

RESOLUTION OF A CARBOXYLIC ACID

BACKGROUND OF THE INVENTION

Pharmacological properties are often dependent on a particular stereochemistry and thus the resolution of a racemic mixture of carboxylic acids containing an alpha chiral carbon is a useful chemical process.

Ruechardt (U.S. Pat. No. 4,691,020) discloses the addition of an optically active alcohol to a ketene, derived from the carboxylic acid analog of the ketene, in the presence of a tertiary amine to yield the respective diastereomeric esters which are converted to the optically active carboxylic acids. Ruechardt describes a preference for 1-aryl $C_{1-4}$ alkan-1-ols, although terpene alcohols such as menthol and certain amino alcohols are also mentioned as suitable. The Ruechardt process employs a trialkylamine generally in a concentration of 0.5 to 1 mole of amine per mole of ketene. However, amounts as low as 0.1 mole amine are said to be sufficient. Ruechardt reports optical yields of not less than 30% and in most cases 70 to 80%.

It is highly preferable in commercial resolution processes to employ a readily available and inexpensive alcohol and obtain optical purities of at least 90%; in this regard the preferred alcohols of Ruechardt may not be as widely available and inexpensive as one might prefer. It is an object of the present invention to prepare optically active carboxylic acids in a more economical and simpler manner and in a higher optical purity than hitherto.

DETAILED DESCRIPTION OF THE INVENTION

The present invention is a process for the preparation of a carboxylic acid of structural formula (I):

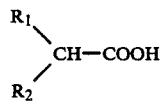

888
wherein:
$R_1$ and $R_2$ are each independently selected from:
a. $C_{1-10}$ alkyl optionally substituted with a group X;
b. $C_{6-10}$ aryl or $C_{7-11}$ araalkyl wherein the aryl moiety is optionally substituted with a group X and optionally contains 1 to 2 heteroatoms such as N, O or S;
c. $C_{5-8}$ cycloalkyl optionally substituted with X;
d. $C_{2-10}$ alkenyl optionally substituted with a group X;
e. $C_{2-10}$ alkynyl optionally substituted with a group X;
f. $C_{1-5}$ alkyloxy;
g. $C_{1-5}$ alkylthio;
provided that $R_1$ and $R_2$ are not identical;
X is H, $C_{1-6}$ alkyl, $C_{1-5}$ alkoxy, halogen, $C_{1-5}$ acyloxy, $C_{1-5}$ acylamino, $C_{1-5}$ acyl or trialkylsiloxy:
which comprises:
reacting a ketene of formula (II):

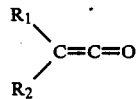

with an optically active α-hydroxyester or an α-hydroxy tertiary amide (ROH) (III) in the presence of up to 10 moles of a tertiary amine (IV) per mole of ketene in a nonpolar solvent at a temperature range between −80° and 25° C., to yield a pair of diastereomeric esters (V):

wherein:
R is the organic radical of the α-hydroxy ester or α-hydroxy tertiary amide, ROH (III); and separating the diastereomeric esters followed by conversion to the carboxylic acids (I).

The groups alkyl, alkenyl or alkynyl as described herein may be straight or branched chain.

The starting ketene of formula (II) contains groups $R_1$ and $R_2$, which may be any groups which allow for a stable ketene and which do not react with the α-hydroxyester (III) provided that $R_1$ and $R_2$ are structurally distinct and neither $R_1$ nor $R_2$ is hydrogen. It will be appreciated by those skilled in the art that some substituent groups, such as hydroxy can be contained in $R_1$ or $R_2$ in a protected form such as by formation of a trialkylsilyloxy moiety. The text by T. W. Greene, *Protective Groups In Organic Synthesis*, John Wiley & Sons, N.Y. (1981) describes general methods of protection. $R_1$ and $R_2$ are preferably $C_{1-6}$ alkyl, $C_{6-10}$ aryl or $C_{7-11}$ araalkyl optionally substituted with a group X, or $C_{5-8}$ cycloalkyl optionally substituted with a group X wherein X is $C_{1-6}$ alkyl, $C_{1-5}$ alkoxy, halogen, $C_{1-5}$ acyloxy, $C_{1-5}$ acyl, $C_{1-5}$ acylamino and trialkyl silyloxy. Further illustrating the groups $R_1$ and $R_2$ are $C_{1-6}$ alkyl, phenyl optionally substituted with X, naphthyl optionally substituted with X, and phenyl $C_{1-3}$ alkyl substituted with X wherein X is $C_{1-6}$ alkyl.

Specifically exemplifying the starting ketene are those compounds (II) wherein:
a. $R_1$ is 4-isobutylphenyl, $R_2$ is $CH_3$;
b. $R_1$ is 4-nitrophenyl, $R_2$ is methyl;
c. $R_1$ is 4-methoxyphenyl, $R_2$ is methyl;
d. $R_1$ is phenyl, $R_2$ is methyl;
e. $R_1$ is phenyl, $R_2$ is ethyl;
f. $R_1$ is 2-(6-methoxynaphthyl), $R_2$ is methyl.

Any optically active α-hydroxyester or α-hydroxy tertiary amide (III) may be employed provided it does not contain groups, other than the hydroxy, which react with the ketene functionality. Preferably the α-hydroxyester is a lactate ester such as an alkyl, phenyl or benzyl lactate ester or an α-hydroxylactone. More preferably the α-hydroxyester is isobutyl, ethyl, methyl, isopropyl or benzyl lactate or pantolactone. Preferably the α-hydroxy tertiary amide is a N,N-di($C_{1-5}$ alkyl)lactamide or a N,N-diaryl-lactamide. More preferably the α-hydroxy tertiary amide is N,N-dimethyllactamide.

Suitable tertiary amines are trialkylamines which may be open chain or cyclic. Preferred amines are tri($C_{1-5}$ alkyl) amines such as trimethylamine, dimethylethylamine, triethylamine, 1,4-diazobicyclo-[2,2,2]-octane (DABCO) or N-methylpyrrolidine. The presence of amine is not critical to the instant process. At temperatures above −45° C. and with an alkyl lactate as the chiral alcohol a diastereomeric ratio of 80:20 was observed in the absence of any amine. It is preferred that the amine be present in a ratio of 0.01 moles to 10 moles of a tertiary amine per mole ketene. It is most preferred that the ratio be 0.01 to 2.0 moles amine per mole ketene.

Suitable solvents for the present reaction are aprotic liquids which are inert to the reacting moieties. Examples of such solvents are hydrocarbons such as hexane, heptane, toluene, or cyclohexane or ethereal solvents such as diethyl ether, tetrahydrofuran, or methyl tert-butyl ether. The preferred solvents are hexane, heptane, and toluene.

In the present process the α-hydroxyester or α-hydroxy tertiary amide (III) is added to a solution of the ketene (II). The mole ratio of ketene to α-hydroxy ester or α-hydroxy tertiary amide may be 1 to 1.5 but preferably is 1 to 1.2, and most preferably is a ratio of approximately 1:1. The addition temperature may be −80° C. to ambient temperature. The preferred temperature is about −75° C. The concentration of ketene may range from 1.0M to 0.01M. The diastereomeric excess (d.e.) is greater at the lower concentrations. The reaction mixture is aged for about 0.5 hours to 2.0 hours and an aliquot assayed by HPLC. At completion the product diastereomeric esters (V) are separated and recovered by standard techniques well known for separating diastereomers such as chromatographic separations and the like. The respective diastereomeric esters may be hydrolyzed to carboxylic acids (I) under acidic hydrolysis conditions such as by dissolving the ester in acetic acid and warming with 6N or 2N HCl. The esters may also be hydrolyzed under basic conditions such as aqueous lithium hydroxide followed by treatment with mineral acid.

Where compound (I) is Ibuprofen the optical purity of the present process is greater than 90% and typically about 97%. With R-pantolactone as the α-hydroxyester the optical purity of Ibuprofen was 100%. (R or S represents configuration.)

It is an advantage of this invention that the employed optically active α-hydroxyesters or α-hydroxy tertiary amides are readily available and inexpensive.

Ketenes (II) are readily prepared from the respective racemic carboxylic acids (I) by standard conversion of the acid to the acid halide followed by reaction of the acid chloride with an amine base to yield ketene (II).

EXAMPLE 1

Preparation of S- Ibuprofen (a) R/S - Ibuprofen acid chloride

In a 500-mL 3-necked flask fitted with a mechanical stirrer, condenser, and thermometer, R/S-Ibuprofen (10.3 g, 50 mmol) was suspended in heptane (105 mL, sieve-dried over 3 A molecular sieves, KF=6.0 mcg/mL). Under a nitrogen atmosphere thionyl chloride (4.0 mL, 55 mol) was added over 5 minutes followed by dimethyl formamide (0.2 mL, 2.5 mmol). The solution was heated at 45°–55° C. for 2.5 hours[1].

[1]The acid chloride formation was monitored by quenching an aliquot of the reaction solution into methanol. The methanol solution was warmed to 50° C. for a few minutes and was assayed by HPLC: Microsorb C-8 4.6 mm×150 mm; 60:40:0.1 acetonitrile-water-trifluoroacetic acid; 1.5 mL/min; 230 nm; Ibuprofen, 3.64 min; Ibuprofen methyl ester, 8.0 min. The formation of the acid chloride was complete when <1 area % of Ibuprofen remained.

(b) S-Ethyl Lactate Esters Of Ibuprofen

The acid chloride was cooled to room temperature and concentrated to 50 mL under vacuum at 40 mbar, 25° C. Heptane (50 mL, sieve-dried) was added and this solution was concentrated to 50 mL. Heptane (∼50 mL) was added to bring the final volume to 100 mL. At room temperature, a solution of trimethylamine (8.85 g, 150 mmol) or dimethylethylamine (16.2 mL, 150 mmol) as a 1M solution in heptane (150 mL) was added as a stream over 10 minutes.

The mixture was stirred at room temperature for 1.5–2 hours.[2]

[2]The formation of the ketene was followed by infrared spectroscopy (IR). A 0.15–0.25 mL aliquot was placed in an IR cell (heptane reference solution). The acid chloride carbonyl peak (1790 cm$^{-1}$) disappeared as the ketene peak (2100 cm$^{-1}$) became more intense. During the reaction and assay some Ibuprofen anhydride was observed by IR (two peaks; 1740 and 1810 cm$^{-1}$).

The solution was cooled to −78° C. S-Ethyl lactate[3] (6.8 mL, 60 mmol) was added dropwise over 10–15 minutes, keeping the reaction solution less than −75° C. The slurry was stirred at −78° to −75° C. for 30 minutes. The diastereomeric ratio of S-Ethyl lactate esters of Ibuprofen was found to be 97:3 S/R[4].

[3]Aldrich S-ethyl lactate was distilled (b.p. 55°–57° C., 13–15 mbar) to remove ethanol and dimeric material. A 10% forecut was discarded and 10% of the material left in the distillation flask.

[4]The reaction was assayed by adding an aliquot of the reaction mixture to methanol (the unreacted ketene was converted to Ibuprofen methyl ester). When <1 area % of the methyl ester was present by HPLC analysis the reaction was complete: Microsorb C-8; 4.6 mm×150 mm; 70:30:0.1 acetonitrile-water-trifluoroacetic acid; 1.5 mL/min; 230 nm; Ibuprofen methyl ester, 4.3 min; S-Ibuprofen S-ethyl lactate ester, 6.0 min; R-Ibuprofen S-ethyl lactate ester, 6.35 min; Ibuprofen anhydride, 23 min (two unresolved peaks of the diastereomers). The diastereoselectivity of the reaction was measured by HPLC analysis: Microsorb C-8; 60:40:0.1 acetonitrile-water-trifluoroacetic acid; 1.5 mL/min; 230 nm; S-Ibuprofen S-ethyl lactate ester; 12.54 min; R-Ibuprofen S-ethyl lactate ester, 13.4 minutes. The mixture of diastereomers was generally in the 96:4 to 97:3 S,S/R,S range.

When the reaction was complete the mixture was warmed to −10° C. and 3-dimethylaminopropylamine[5] (0.63 mL, 5.0 mmol) was added. The mixture was warmed to room temperature.

[5]Before the diastereomeric esters were hydrolyzed it was necessary to remove Ibuprofen anhydride, if it had been formed. Typically, 2–5 area % of this by-product was formed in the reaction due to residual water in the reaction materials. 3-Dimethyl-amino-propylamine was added in 100mol % excess relative to the area % of Ibuprofen anhydride present in the reaction mixture. Microsorb C-8 4.6 mm×150 mm; 70:30:0.1 acetonitrile-water-trifluoroacetic acid; 1.5 mL/min; 230 nm; esters, 5.5 min; anhydride, 20 minutes.

(c) S-Ibuprofen

To the white slurry from step (1b) was added 2N aqueous hydrochloric acid (100 mL) as a stream over 5 minutes. The temperature was maintained at 20°–25° C. The mixture was well-stirred for 15 minutes and the layers were separated. The heptane solution was washed with 1M aqueous trimethylamine (100 mL). The layers were separated and the heptane solution was washed with water (50 mL). Acetonitrile (125 mL) was added and the mixture was cooled to 0° C. A solution of lithium hydroxide monohydrate (6.3 g, 150 mmol) in water (125 mL) was added over 5 minutes, maintaining the reaction temperature at 0°–5° C. The two-phase mixture was vigorously stirred at 5° C. for 16 hours or until the saponification[6] was complete.

[6]The saponification of the esters was followed by HPLC: Microsorb C-8, 70:30:0.1 acetonitrile-water-trifluoroacetic acid; 1.5 mL/min, 230 nm; Ibuprofen, 2.4 min; Ibuprofen-lactic acid ester, 2.9 min; S- and R-Ibuprofen S-ethyl lactate esters, 5.8 and 6.1 min, respectively. The reaction was complete when <1 area % of the esters and half-ester remained.

The mixture was warmed to room temperature and the layers were separated. The heptane layer was washed with water (100 mL). Hexane (250 mL) was added to the combined aqueous layers and 6N aqueous hydrochloric acid (25–30 mL) was added keeping the temperature <25° C. The mixture was well-stirred and the layers separated. The aqueous layer (lower) was washed with hexane (50 mL). The combined hexane layers were washed with water (50 mL) and the hexane solution concentrated to dryness. Ibuprofen was obtained as a white solid as a 94.5:5.5 S/R-mixture of enantiomers.[7]

[7]The chiral assay of the free acid was run by dissolving a 20-mg sample in isopropyl acetate (2 mL, sieve-dried) in a 10 mL round bottomed flask. Carbonyl diimidazole (1.0 mL as a 0.1M solution in isopropyl acetate) was added and the mixture was stirred for 15 minutes at room temperature. Benzyl amine (11.7 mcL) was added via syringe and the solution was stirred at room temperature for 30–60 minutes. The isopropyl acetate solution was transferred to a separatory funnel and rinsed over with 3 mL isopropyl acetate. There it was washed with 2N aqueous hydrochloric acid (10 mL), 5% aqueous sodium bicarbonate (10 mL), and brine (10 mL). The isopropyl acetate layer (upper) was passed through a silica-gel cartridge (Sep-Pak, Whatman) and the cartridge was rinsed with isopropyl acetate (5 mL). The combined eluents were concentrated to dryness and the residue dissolved in hexanes-isopropanol (9:1, 20 mL). The sample was assayed for chirality on a Pirkle L-Phenylglycine Covalent column (Regis); 97:3 hexanes-isopropanol; 1.8 mL/min; 230 nm; R-Ibuprofen benzamide, 15.5 min; S-Ibuprofen benzamide, 17.7 minutes.

EXAMPLES 2–7

The following esters of structural formula (V) were prepared as enriched diastereomeric pairs, following the general procedure of Example 1, but substituting equivalent amount of the appropriate acid chloride in Step 1b, and employing an equivalent amount of an alkyl lactate or a lactamide and the solvent as indicated below.

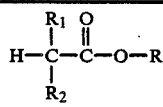

| $R_1$ | $R_2$ | ROH | SOLVENT | RATIO OF DIASTEREOMERS |
|---|---|---|---|---|
| 4-isobutylphenyl | methyl | S-ethyl lactate | toluene | 94:6 SS/RS |
| 4-isobutylphenyl | methyl | R-isobutyl lactate | toluene | 94:6 RR/SR |
| 4-isobutylphenyl | methyl | S-N,N-dimethyl-lactamide | hexane | 94:6 SS/RS |
| 4-nitrophenyl | methyl | S-ethyl lactate | toluene | 92.7:7.3 SS/RS |
| 4-nitrophenyl | methyl | R-isobutyl lactate | toluene | 95:5 RR/SR |
| 4-methoxyphenyl | methyl | S-ethyl lactate | toluene | 93:3 6.7 SS/RS |
| 4-methoxyphenyl | methyl | R-isobutyl lactate | toluene | 93.6:6.1 RR/SR |
| phenyl | methyl | S-ethyl lactate | toluene | 93.8:6.2 SS/RS |
| phenyl | methyl | R-isobutyl lactate | toluene | 94.0:6.0 RR/SR |
| phenyl | ethyl | S-ethyl lactate | toluene | 95.1:4.9 SS/RS |
| 2-(6-methoxynaphthyl) | methyl | S-ethyl lactate | toluene | 90:10 SS/RS |
| 2-(6-methoxynaphthyl) | methyl | R-isobutyl lactate | toluene | 89.5:10.5 RR/SR | c. $C_{5-8}$ cycloalkyl substituted with X;
d. $C_{2-10}$ alkenyl substituted with a group X;
e. $C_{2-10}$ alkynyl substituted with a group X;
f. $C_{1-5}$ alkyloxy;
g. $C_{1-5}$ alkylthio; provided that $R_1$ and $R_2$ are not identical;

R is the organic radical of an α-hydroxy ester or α-hydroxy tertiary amide (ROH) (III);

X is H, $C_{1-6}$ alkyl, $C_{1-5}$ alkoxy, halogen, $C_{1-5}$ acyloxy, $C_{1-5}$ acylamino, $C_{1-5}$ acyl, trialkylsiloxy;

which comprises:

reacting a ketene of formula (II):

with an optically active α-hydroxy ester or α-hydroxy tertiary amide (ROH) (III) in a nonpolar solvent in the presence of up to 10 moles tertiary amine (IV) per mole ketene at a temperature between −80° and 25° C. to yield an optically active ester (V).

2. A process according to claim 1 wherein the mole ratio of amine (IV) to ketene is 0.01 to 1.0 moles amine to 1 mole ketene.

3. A process according to claim 2 wherein $R_1$ and $R_2$ independently are selected from $C_{1-6}$ alkyl, $C_{6-10}$ aryl, $C_{7-11}$ aralkyl, or $C_{5-8}$ cycloalkyl all substituted with a group X;

X is H, $C_{1-6}$ alkyl, $C_{1-5}$ alkoxy, halogen, $C_{1-5}$ acyloxy, $C_{1-5}$ acyl, $C_{1-5}$ acylamino, or trialkylsilyloxy.

4. A process according to claim 3 wherein: $R_1$ and $R_2$ independently are selected from: $C_{1-6}$ alkyl, phenyl or phenyl $C_{1-3}$ alkyl wherein the phenyl moiety is optionally substituted with X;

What is claimed is:

1. A process for the preparation of an optically active ester (V) or an enriched mixture therein:

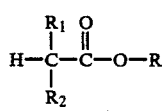

wherein $R_1$ and $R_2$ are independently selected from:
a. $C_{1-10}$ alkyl substituted with a group X;
b. $C_{6-10}$ aryl or $C_{7-11}$ araalkyl wherein the aryl moiety is substituted with a group X X is $C_{1-6}$ alkyl.

5. A process according to claim 4 wherein:
   a. $R_1$ is 4-isobutylphenyl, $R_2$ is $CH_3$;
   b. $R_1$ is 4-nitrophenyl, $R_2$ is methyl;
   c. $R_1$ is 4-methoxyphenyl, $R_2$ is methyl;
   d. $R_1$ is phenyl, $R_2$ is methyl;
   e. $R_1$ is phenyl, $R_2$ is ethyl;
   f. $R_1$ is 2-(6-methoxynaphthyl), $R_2$ is methyl.

6. A process according to claim 5 wherein the optically active alcohol is a α-hydroxyester (ROH) selected from a $C_{1-5}$ alkyl, phenyl or benzyl lactate or a α-hydroxy lactone.

7. A process according to claim 6 wherein the α-hydroxyester (ROH) is methyl, ethyl, isopropyl, isobutyl or benzyl lactate.

8. A process according to claim 7 wherein the α-hydroxyester (ROH) is S(−) ethyl lactate and the compound (V) produced is the S-ethyl lactate ester of S-Ibuprofen.

9. A process according to claim 7 wherein the α-hydroxyester (ROH) is R(+)-isobutyl lactate and the compound (V) produced is the R-isobutyl lactate ester of R-Ibuprofen.

10. A process according to claim 6 wherein the α-hydroxy ester (ROH) is R(−)-pantolactone and the compound (V) produced is the ester of R(−)-Ibuprofen wherein:

R is 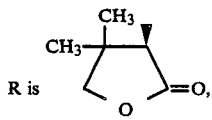

11. A process according to claim 5 wherein the optically active alcohol (ROH) is a α-hydroxy tertiary amide selected from a N,N-di($C_{1-5}$ alkyl) lactamide or a N,N-diaryllactamide.

12. A process according to claim 10 wherein the α-hydroxy tertiary amide (ROH) is a S-N,N-dimethyllactamide and the compound (V) produced is the S-N,N-dimethyllactamide ester of S-Ibuprofen.

13. A process according to claim 8 in which the tertiary amine is selected from trimethylamine, dimethylethylamine, triethylamine or 1,4-diazobicyclo-[2,2,2]-octane and the nonpolar solvent is selected from hexane, heptane, toluene, cyclohexane, diethyl ether, tetrahydrofuran or methyl-tert-butyl ether.

14. A process according to claim 13 in which the tertiary amine is trimethylamine or dimethylethylamine and the solvent is hexane, heptane, or toluene and the temperature is about −75° C.

15. A process according to claim 9 in which the tertiary amine is selected from trimethylamine, dimethylethylamine, triethylamine or 1,4-diazobicyclo-[2,2,2]-octane and the nonpolar solvent is selected from hexane, heptane, toluene, cyclohexane, diethyl ether, tetrahydrofuran or methyl-tert-butyl ether.

16. A process according to claim 15 in which the tertiary amine is trimethylamine or dimethylethylamine and the solvent is hexane, heptane or toluene, and the temperature is about −75° C.

17. A process according to claim 10 in which the tertiary amine is selected from trimethylamine, dimethylethylamine, triethylamine or 1,4-diazobi-cyclo-[2,2,2]-octane and the nonpolar solvent is selected from hexane, heptane, toluene, cyclohexane, diethyl ether, tetrahydrofuran or methyl-tert-butyl ether.

18. A process according to claim 17 in which the tertiary amine is trimethylamine or dimethylethylamine, the solvent is toluene and the temperature is about −75° C.

19. A process according to claim 12 in which the tertiary amine is trimethylamine, the solvent is hexane and the temperature is about −75° C.

20. A process of claim 1 which further comprises hydrolysis of the ester (V) to form carboxylic acid (I).

21. A process of claim 20 wherein the hydrolysis is conducted in an acidic medium.

22. A process of claim 20 wherein the hydrolysis is conducted in a basic medium.

* * * * *